United States Patent
Worstell

(10) Patent No.: US 10,231,679 B2
(45) Date of Patent: Mar. 19, 2019

(54) PROTON RADIOGRAPHY SYSTEM INCORPORATING TIME-OF-FLIGHT MEASUREMENT

(71) Applicant: Incom, Inc., Charlton, MA (US)

(72) Inventor: William Alan Worstell, Wayland, MA (US)

(73) Assignee: Incom, Inc., Charlton, MA (US)

(*) Notice: Subject to any disclaimer, the term of this patent is extended or adjusted under 35 U.S.C. 154(b) by 163 days.

(21) Appl. No.: 15/456,795

(22) Filed: Mar. 13, 2017

(65) Prior Publication Data
US 2017/0258421 A1 Sep. 14, 2017

Related U.S. Application Data

(60) Provisional application No. 62/306,873, filed on Mar. 11, 2016.

(51) Int. Cl.
| | |
|---|---|
| A61B 6/03 | (2006.01) |
| A61N 5/10 | (2006.01) |
| A61B 6/00 | (2006.01) |

(52) U.S. Cl.
CPC ............ *A61B 6/032* (2013.01); *A61B 6/4071* (2013.01); *A61B 6/4258* (2013.01); *A61N 5/10* (2013.01); *A61N 5/103* (2013.01); *A61N 5/1071* (2013.01); *A61N 2005/1087* (2013.01)

(58) Field of Classification Search
CPC .......... A61N 2005/1087; A61N 5/1071; A61N 5/10; A61N 5/103; A61B 6/032; A61B 6/4258; A61B 6/4071
See application file for complete search history.

(56) References Cited

PUBLICATIONS

A. Kraan, "Range Verification Methods in Particle Therapy: Underlying Physics and Monte Carlo Modeling", Frontiers in Oncology, Jul. 7, 2015.
J. Schuemann et al., "Site-specific range uncertainties caused by dose calculation algorithms for proton therapy", Phys. Med. Biol. Aug. 7, 2014.
H. Paganetti, "Range uncertainties in proton therapy and the role of Monte Carlo simulations", Phys. Med. Biol. Jun. 7, 2012.
G. Poludniowski et al., "Proton radiography and tomography with application to proton therapy", Br. J. Radiol, Sep. 2015.
(Continued)

*Primary Examiner* — David P Porta
*Assistant Examiner* — Faye Boosalis
(74) *Attorney, Agent, or Firm* — BainwoodHuang

(57) ABSTRACT

A proton radiography system includes a source of a proton beam at nonrelativistic energy, directed on a beam path to an object to be imaged; one or more time-of-flight (TOF) detectors arranged on the beam path to detect incidence of beam protons and generate output signals indicative thereof with a time resolution substantially less than a time of flight of the protons; and a data acquisition and analysis subsystem coupled to the TOF detectors to receive the respective output signals and (1) calculate TOF values for respective bunches of one or more protons, (2) convert the TOF values to proton velocity values and proton energy values, and (3) use the proton energy values to calculate a corresponding value for a physical property of the object along the beam path, and incorporate the value into elements of a radiographic image of the object stored or displayed in the system.

14 Claims, 7 Drawing Sheets

(56) References Cited

PUBLICATIONS

G. Poludniowski et al., "Proton-counting radiography for proton therapy: a proof of principle using CMOS APS technology", Phys. Med. Biol. Jun. 7, 2014.

M. Testa et al., "Proton radiography and proton computed tomography based on time-resolved dose measurements", Phys. Med. Biol. Nov. 21, 2013.

H. Sadrozinski et al., "Development of a Head Scanner for Proton CT", Nuclear Instruments and Methods in Physics Research, A, Jan. 21, 2013.

B. Marchard et al., "IBA proton pencil beam scanning: an innovative solution for cancer treatment", Proceedings of EPAC, Jan. 2000.

J. Flanz, "Accelerators for charged particle therapy", Modern Physics Letters A, vol. 30, No. 17, (2015).

C. Morris et al, "New Developments in Proton Radiography at the Los Alamos Neutron Science Center (LANSCE)", Experimental Mechanics, Dec. 30, 2015.

M. Kisielinski and J. Wojtkowska, "The proton beam energy measurement by a time-of-flight method", Nukleonika, 2007.

D. C. Williams, "The Most Likely Path of an Energetic Charged Particle Through a Uniform Medium", Phys. Med. Biol. Jul. 7, 2004.

M. Minot et al., "Pilot production & commercialization of LAPPD", Nuclear Instruments and Methods in Physics Research A 787, Jul. 2015, p. 78-84.

E. Oberla et al., "A 15 GSa/s, 1.5 GHz bandwidth waveform digitizing ASIC", Nuclear Instruments and Methods in Physics Research A 735, 2014, pp. 452-461.

B. Adams et al., "Measurements of the Gain, Time Resolution, and Spatial Resolution of a 20x20 cm2 MCP-based Picosecond Photo-Detector", Nuclear Instruments and Methods in Physics Research, A 732, 2013, pp. 392-396

B. Adams et al., "A test facility for large-area microchannel plate detector assemblies using a pulsed sub-picosecond laser", Review of Scientific Instruments, 84, 061301, 2013.

L. Brianza et al., "Response of microchannel plates to single particles and to electromagnetic showers", Nuclear Instruments and Methods in Physics Research, A 797, 2015.

PROTON RADIOGRAPHY SYSTEM INCORPORATING TIME-OF-FLIGHT MEASUREMENT

BACKGROUND

The invention is related to the field of radiography using protons or light ions (generally hadrons), referred to herein as "proton radiography".

A principal application of medical proton radiography is for deriving patient-specific proton stopping power images with which to guide proton therapy treatment planning. The principal advantage of proton and light ion therapy (collectively, "hadrotherapy") relative to conventional X-ray photon-based radiation therapy is the ability to more precisely shape the dose delivery profile so as to intensely irradiate target tissue while sparing non-target organs at risk. This is typically performed using the sharply falling distal edge of the Bragg peak, where hadrons deposit rapidly increasing amounts of energy in target tissue before suddenly coming to a stop, thereby sparing tissues beyond the stopping point.

In present practice, the ideal capability of proton therapy is undercut by insufficient knowledge of precisely where this stopping point occurs along a given line-of-incidence within a given patient for an incident proton beam with a defined initial energy. Current treatments typically employ treatment-planning X-ray CT scans, but this is not ideal. X-ray stopping power is generally correlated with but not precisely equivalent to proton stopping power, and a particular patient's anatomy may have changed between treatment planning scans and treatment delivery sessions. Information confirming expected proton stopping power along a line of response for a given patient could instead be obtained by increasing proton incident energy so as to generate a proton beam capable of transmission through the patient and out the patient's opposite side, with the residual proton energy measured after exiting the patient. Subtracting this transmitted proton remaining ("residual") energy from the incident energy then gives information on the proton stopping power along the line of incidence. This is proton transmission radiography, and by combining a complete set of lines of response across the patient one could perform proton computed tomography (pCT) to form a 3-dimensional slice image of the proton stopping power throughout an entire slice through the patient.

Proton radiography and proton CT, despite their acknowledged potential utility for proton radiation therapy planning and potential dose delivery modifications during a proton therapy delivery session, are not presently in widespread clinical use. This is largely because prototype proton radiography designs to date are bulky, rate- and flux-limited, slow, expensive, and difficult to incorporate into the clinical environment.

A review article by Poludniowski G, Allinson N M, and Evans P M entitled "Proton radiography and tomography with application to proton therapy." Br J Radiol 2015; 88. 20150134, describes that a proton transmission radiograph can be obtained by directing a proton beam through an object and onto a suitable sensor. The passage of protons is detected indirectly, typically exploiting its transfer of energy via ionization and excitation. The definition of proton-integrating technology is that signal (e.g. in a pixel) is due to the passage of an undetermined number of incident protons. The resulting signal will depend on both proton fluence and energy distribution, but proton integrating radiography assumes that the signal can be calibrated to average proton water equivalent path length (WEPL) through the patient. The limitations of the proton-integrating approach arise from the interplay of multiple Compton scattering (MCS) and energy loss effects, resulting in a "halo" effect at material interfaces. The degradation in spatial resolution for integrating compared with tracking systems will depend on the patient anatomy and the detector-patient geometry.

The above-referenced review describes both proton-integrating radiography systems and proton-tracking systems. By contrast to proton-integrating devices, proton-tracking radiography and tomography systems consist of a number of position-sensitive detector (PSD) modules to infer proton path (typically between one and four), as well as a residual energy range detector (RERD) to determine proton residual energy. The precision of WEPL determination can be improved by increasing the number of protons in an acquisition. The standard error on an estimate of WEPL will decline by the square root of the number of protons measured. Increasing proton number does, however, increase patient imaging dose and scan acquisition time The above review article lists ten current and recent proton radiography (pRG)/proton CT (pCT) prototypes. In particular, the review article identifies several types of residual energy-range detector technology as follows: Plastic scintillator telescopes (including "hybrid" devices), NaI (Tl) or CSi(Tl) or YAG:Ce calorimeters, x-y Sci-Fi [Scintillating Fiber] arrays, and CMOS APS [Active Pixel Sensor] telescopes. A calorimeter is described as determining the energy of the outgoing proton and therefore accurately determining its state immediately after traversing the patient. In a range telescope, however, only the stopping depth of the proton is determined. Since there will be statistical variations in penetration depth within the range telescope itself (residual range straggling) this will contribute extra uncertainty on the estimate of WEPL [Water Equivalent Path Length]. While this is true, a calorimeter will in fact always possess a finite energy resolution. In addition, calorimeters have the fundamental limitation that when applied to newer proton-beam delivery systems (e.g. synchrocyclotrons and other systems with small delivery "duty cycles") that deliver temporally narrow "bunches" of protons rather than individual protons separated in time, the calorimeter response varies in proportion to the uncertain and variable number of protons in each individual "bunch", In consequence, the superiority of any particular RERD [Residual Energy-Range Detector] over another cannot be established based on such a general criterion.

In addition to limited accuracy, the calorimeter, range telescope, and hybrid technologies described in the review article suffer from the following additional deficiencies: cost, complexity, sensitivity to radiation damage, and bulky volumes incompatible with treatment delivery and patient positioning geometries. An additional deficiency of the above technologies is their limited speed both for detection and for readout, which drives up cost and complexity by requiring fine segmentation to avoid requiring low proton beam fluxes and consequent overlong radiographic scan times.

SUMMARY

Disclosed are apparatus and methods for determining non-relativistic proton transmission information (including but not limited to residual energy after traversing a patient) using precision time-of-flight measurement, principally within the context of a proton radiography system such as a medical proton radiography system. Proton radiography systems incorporating precision time-of-flight information, in particular for proton residual energy determination, show promise to lower proton radiography system complexity and cost, speed image acquisition time while improving image quality, and reduce system bulk and thereby improving compatibility with clinical proton therapy delivery system geometries and workflow.

In one aspect, a proton radiography system is disclosed that includes a source of a beam of protons at nonrelativistic energies, the beam to be directed on a beam path to an object to be imaged; one or more time-of-flight detectors arranged on the beam path, the time-of-flight detectors operative to detect incidence of protons of the beam and to generate respective output signals indicative thereof with a time resolution substantially less than a time of flight of the protons along the beam path; and a data acquisition and analysis subsystem coupled to the time-of-flight detectors to receive the respective output signals and (1) calculate one or more time-of-flight values for respective bunches of one or more protons, (2) convert the time-of-flight values to proton velocity values and corresponding proton energy values, and (3) use the proton energy values to calculate a corresponding value for a physical property of the object along the beam path, and incorporate the value of the physical property into elements of a radiographic image of the object stored or displayed in the proton computed radiography system. Such elements may include responses along individual previously determined lines-of-response and be used for treatment plan verification directly, without requiring the generation of a complete proton radiographic image. In other words, the term "radiographic image" used herein extends to representations of responses along a potentially small number of lines-of-response, which can be seen as partial images of the object.

The detectors may include an upstream pair of detectors between the source and the object, and a downstream pair of detectors downstream from the object, the upstream pair of detectors forming a first imaging telescope whose output signals indicate both location and timing of protons before encountering the object, the downstream pair of detectors forming a combination second imaging telescope and residual energy detector whose output signals indicate both location and timing of protons after encountering the object. The first pair of detectors may be first time-of-flight position-sensitive detectors, and the second pair of detectors second time-of-flight position-sensitive detectors. Either or both the first time-of-flight position-sensitive detectors and the second time-of-flight position-sensitive detectors may be Large Area Picosecond Photon Detectors, which may include respective microchannel plates each having a large array of openings for passage of protons. The microchannel plates may be configured for operation in an ionization mode in which protons are detected by detecting secondary emission of electrons at respective surfaces of the microchannel plates.

An alternative detector configuration may be employed which uses "pencil beam" proton beam delivery to define incident proton beam position, incident direction, and energy, with or without an upstream fast timing detector detecting individual proton or proton bunch incident time. Downstream of the object, this system would use a fast timing detector pair (with or without imaging capability) to determine individual proton or proton bunch residual energies based on individual proton or proton bunch time-of-flight measurements. As with the above-described embodiments, such a system may employ position-sensitive readout of microchannel plates operating in ionization mode to generate fast timing images of individual protons or proton bunches.

Other aspects and alternatives are presented in the detailed description below.

DETAILED DESCRIPTION

Figure 1:
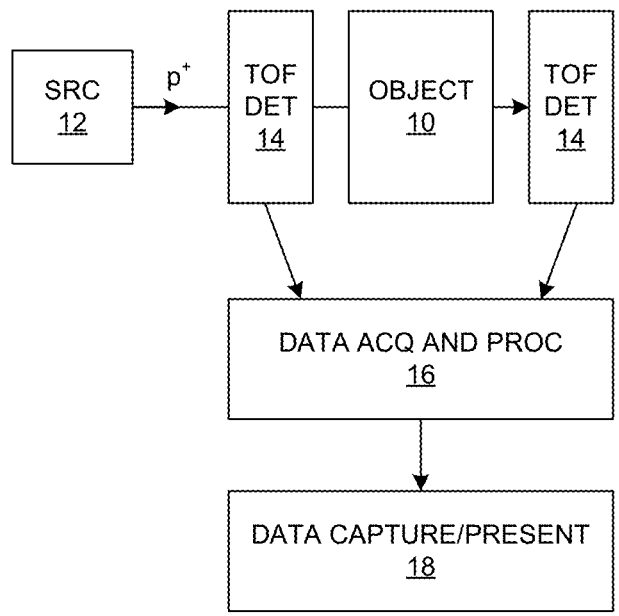
FIG. 1 shows a proton computed radiography system.

FIG. 1 shows a proton computed radiography system for obtaining a radiographic image of an object 10, which in a medical application may be part of a human body for example. The system includes a source 12 of a proton beam $p^+$, one or more time-of-flight (TOF) detectors 14, a data acquisition and analysis subsystem 16, and a data capture and/or presentation subsystem 18. In this description, reference to a "proton" beam is to be understood as encompassing light-ion beams as well. Although FIG. 1 shows both an upstream detector 14 (at left) and a downstream detector 14 (at right), as explained below, both are not necessarily required in all embodiments.

Figure 2:
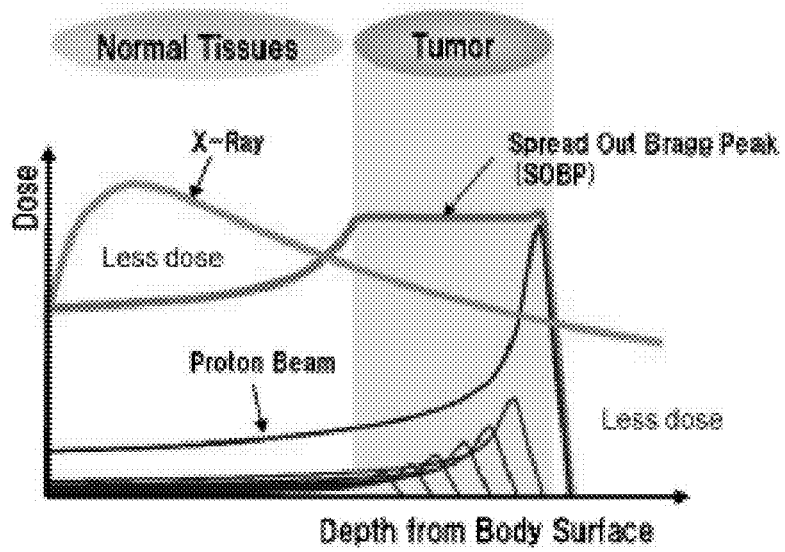
FIG. 2 is a plot of dose versus depth for X-rays and proton beams.

FIG. 2 illustrates the above-referenced advantage of proton and light ion therapy relative to conventional X-ray photon-based radiation therapy, namely its ability to more precisely shape the dose delivery profile so as to intensely irradiate target tissue while sparing non-target organs at risk. This is typically performed using a sharply falling distal edge of the Bragg peak, where hadrons deposit rapidly increasing amounts of energy in target tissue before suddenly coming to a stop, thereby sparing tissues beyond the stopping point. The disclosed technique can provide information confirming expected proton stopping power along a line of response by using a proton beam of sufficient energy to be capable of transmission through the patient and out the patient's opposite side, with the residual proton energy measured after exiting the patient. Subtracting this transmitted proton residual energy from the incident energy then gives information on the proton stopping power along the line of incidence.

Figure 3:
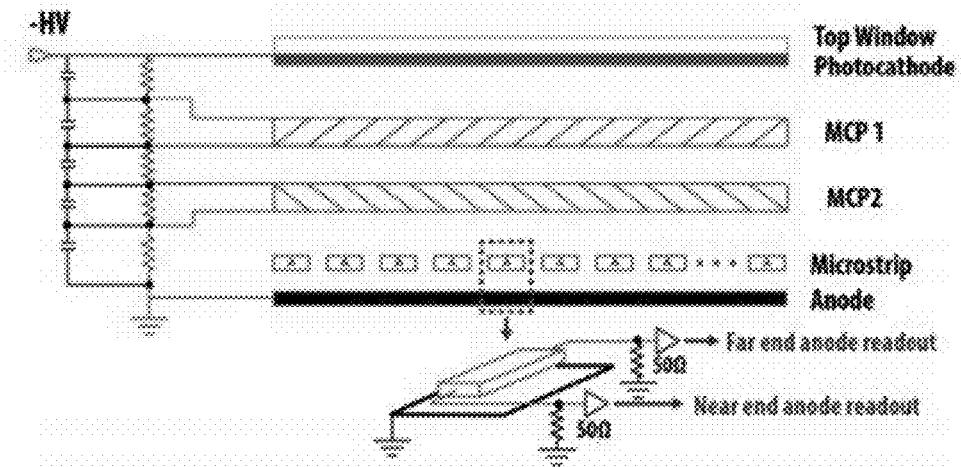
FIG. 3 is a schematic diagram of a large-area picosecond photodetector (LAPPD)

FIG. 3 is a schematic illustrating a particular type of detector 14 known as a Large Area Picosecond Photon Detector or LAPPD. As shown, it includes two parallel microchannel plates MCP 1 and MCP 2. Although a photocathode is also depicted, embodiments may instead be operated in "ionization mode" as explained more below. It also includes a microstrip (or strip) delay line anode readout as TOF detector.

Figure 4:
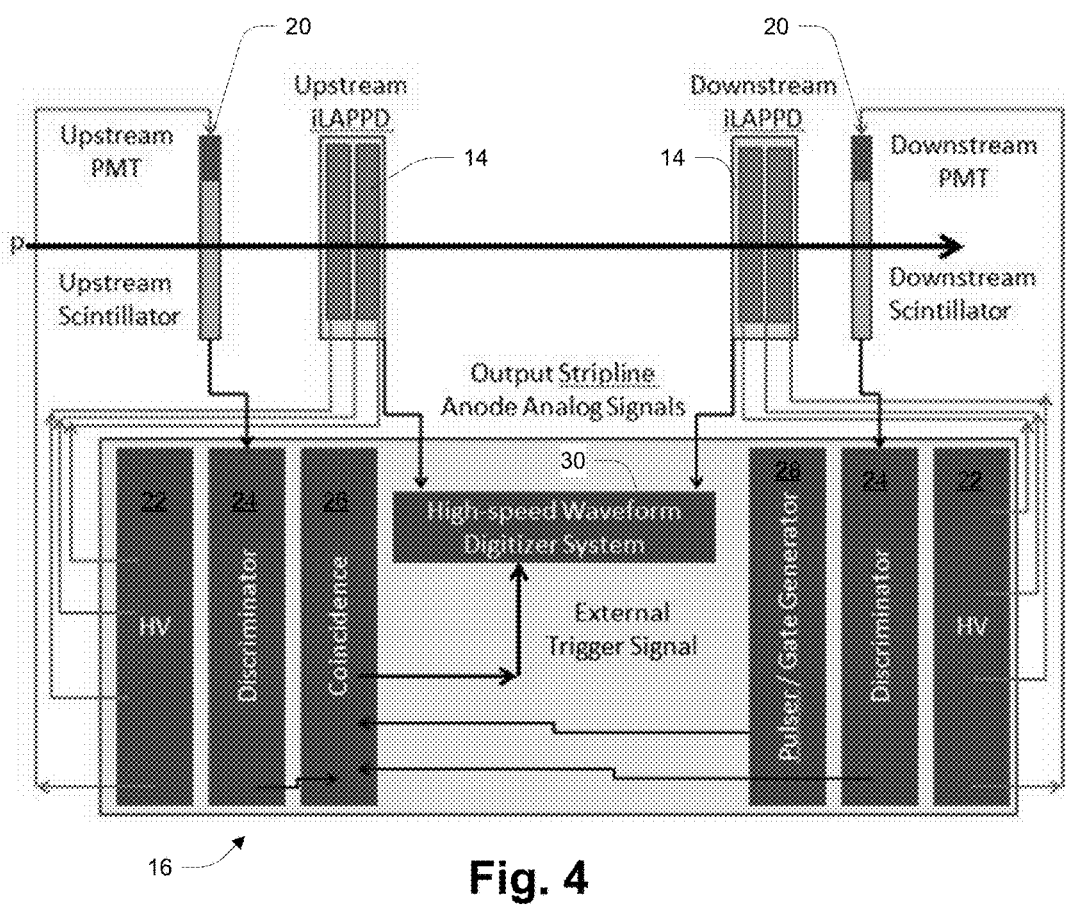
FIG. 4 is a block diagram of the system showing more detail of the data acquisition and analysis subsystem.

FIG. 4 shows a more detailed schematic of the system including power and signal processing for external triggering. In addition to the detectors 14, upstream and downstream photomultiplier tubes (PMTs) 20 are used to generate triggering signals for data capture by the digital acquisition and analysis subsystem 16. That subsystem includes the following components as shown:

High voltage circuitry (HV) 22
Discriminator 24
Coincidence detector 26
Pulse/Gate generator 28
High-speed Waveform Digitizer 30

The coincidence detector 26 generates a trigger signal for use by the high-speed waveform digitizer 30 to capture the output signals from the detectors 14. Note that self-triggering LAPPD readout electronics configurations which do not require the generation of an external trigger are also obtainable.

Figure 5:
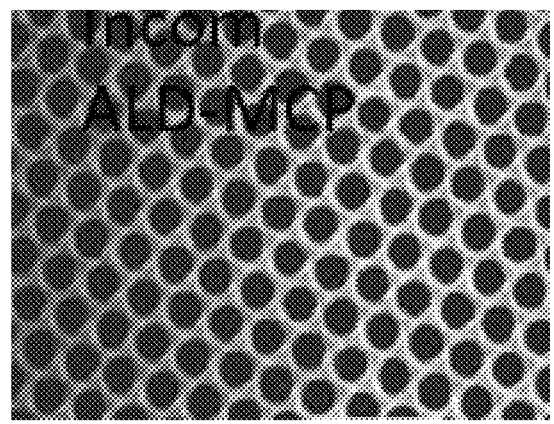
FIG. 5 is a plan view of a portion of a microchannel plate.

FIG. 5 shows a small section of a microchannel plate MCP. It consists of a large, regular array of fused-together capillaries having central openings or channels. The width of the MCP into the paper, which defines the length of the channels, can be on the order of 1 mm to several cm. The MCP may be coated with a material capable of producing or enhancing secondary emission in response to incident protons and the relatively high-energy electron secondaries (delta rays) that they can produce while traversing the MCP. Such secondary emitted electrons are then amplified by multiplication within the MCP structure to result in measurable signals with high time resolution at the MCP output.

Figure 6:
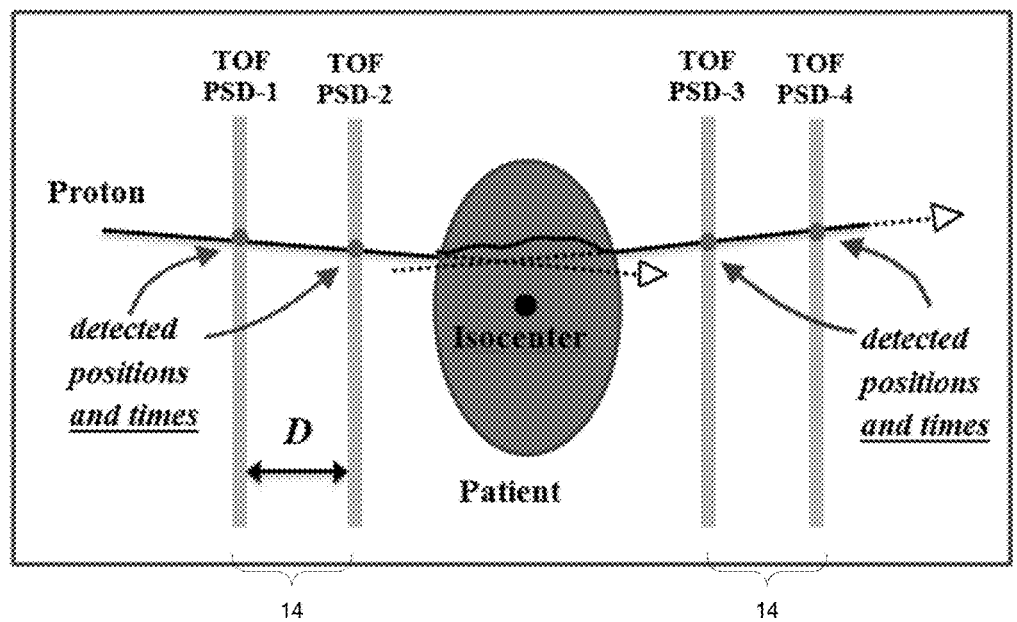
FIG. 6 is a schematic illustration of a proton radiography system according to a first embodiment.

FIG. 6 presents an illustrative first embodiment of a time-of-flight proton radiography/proton CT system, employing an upstream time-of-flight imaging telescope (combination of TOF PSD-1 and TOF PSD-2) and downstream combination imaging telescope and time-of-flight residual energy detector (combination of TOF PSD-3 and TOF PSD-4). The data acquisition and analysis subsystem 16 and data capture/presentation subsystem 18 (FIG. 1) are omitted for simplicity. As shown, the TOF PSDs generate output signals indicative of detected positions as well as detected times. The output signals are provided to the data acquisition and analysis subsystem 17 which uses the timing and position information to measure a parameter [residual energy, information bearing on most likely path] of the charged particles traversing the object being imaged.

Conventional tracking proton radiography systems use a bulky and expensive range stack or calorimeter to determine individual proton residual energies, while in the embodiment of FIG. 6 precision time-of-flight measurement between two imaging detectors is used to perform this function as shown. Advantages are a more compact, lower cost, and less expensive system with higher performance. The timing accuracy of the time-of-flight (TOF) measurement scales linearly with the physical separation of the TOF PSDs, while the residual energy measurement is a strongly nonlinear function of the time-of-flight measurement, with greatest accuracy at lowest energies corresponding to slowest velocities and longest flight times after proton traversal of the patient.

The above configuration may be use with either with single protons or with temporally and spatially coherently proton bunches. This can be used both for residual energy imaged measurement to complement spatial, temporal, and energetic beam modulation strategies, as well as to provide a measurement of ensemble average energy loss without requiring resolved individual protons as with a calorimeter or range stack. By using fast time-of-flight detectors with narrow pulse widths, the achievable readout rate (and hence reduction in time and dose associated with image acquisition) can far exceed what is possible with integrating approaches. Finally, by providing an additional dimension of finely-resolved spatial resolution in pulse shapes, one gains a means for preferentially weighting less-scattered proton paths without requiring explicit proton tracking.

Note that the same method would work for light ions, with still greater accuracy because of their lower velocities. Flight paths between upstream and downstream TOF-PSDs encode multiple path-integrated energy losses into time-of-flight delays which could be deconvolved from up/downstream timing distributions.

In one implementation, the mean values for these time-of-flight distributions, which are readily obtainable with high accuracy using available waveform digitizing electronics, would suffice to measure mean residual energy for single protons or for proton bunches, including the effects of multiple scattering. This measurement combined with predictions obtainable using proton therapy planning software (e.g., Monte Carlo-based proton therapy planning software) is capable of providing precise verification of physical assumptions (including patient anatomy and stopping power) underlying precision treatment planning software calculations. This verification can be collected at the time of treatment delivery, and can thereby contribute to treatment dose delivery quality control.

Figure 7A:
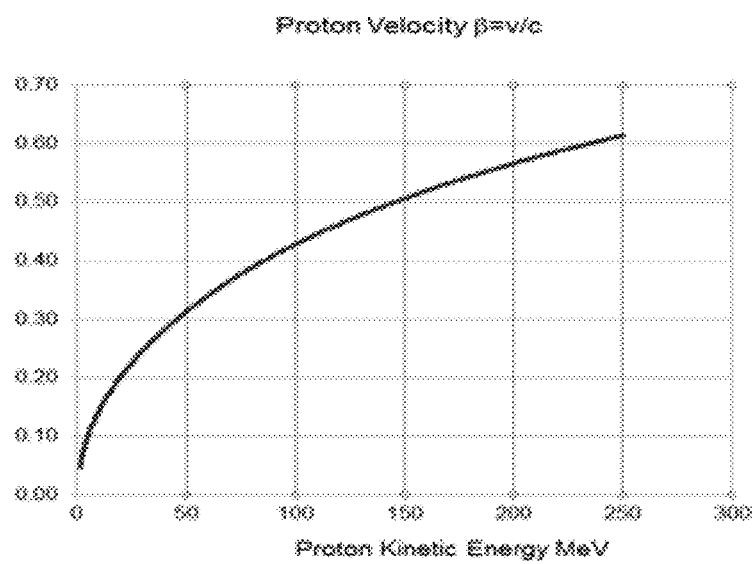
FIGS. 7A-7D are plots of various kinetic properties of protons in the system.
Figure 7B:
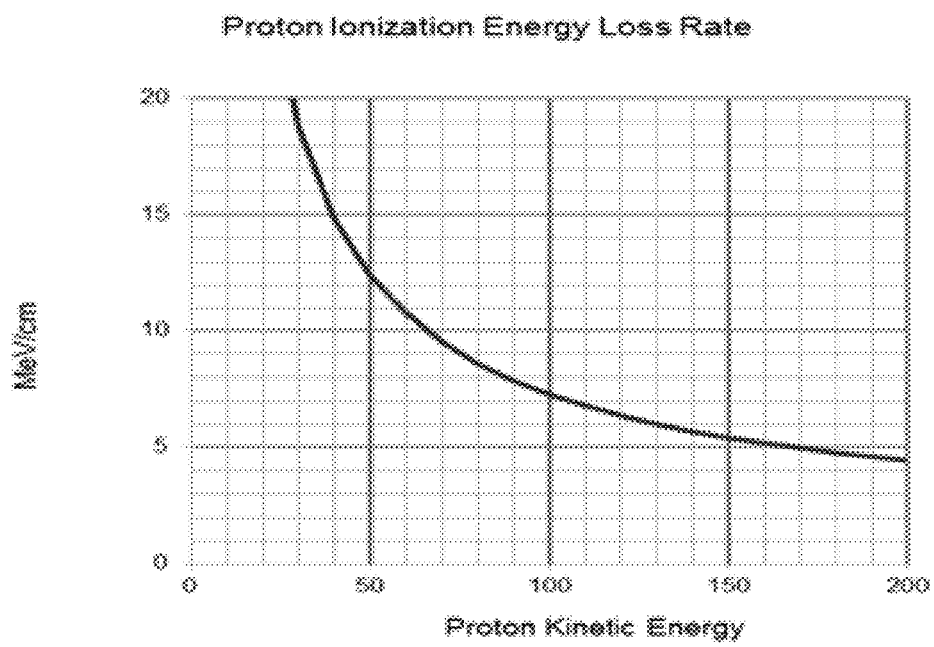
Figure 7C:
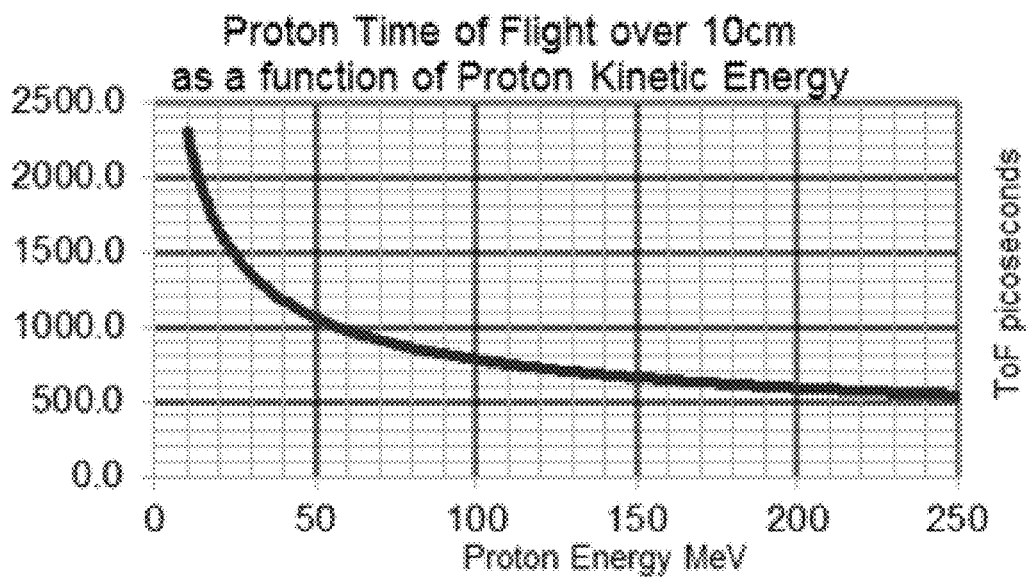
Figure 7D:
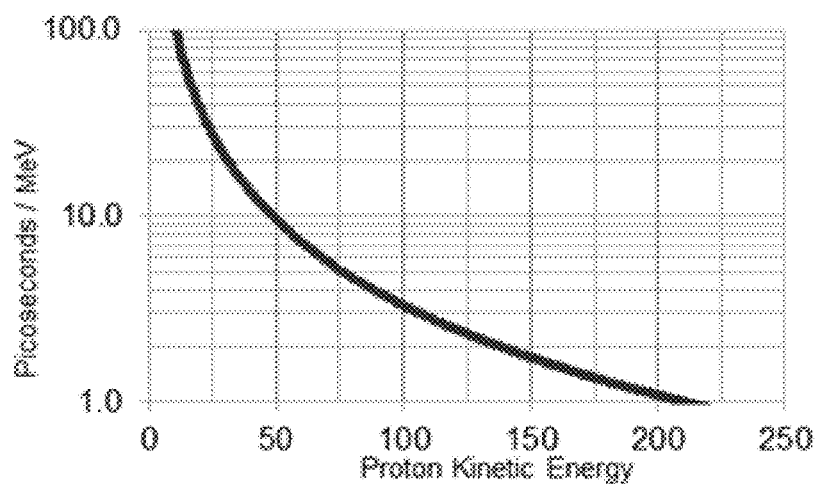

FIGS. 7A-7D provide information regarding the kinematics of protons at proton therapy beam energies, showing the ionization and time-of-flight dependence on kinetic energy. FIG. 7A shows proton velocity as a function of kinetic energy. FIG. 7B shows proton ionization energy loss rate as a function of kinetic energy in MeV. FIG. 7C shows proton time of flight across a 10 cm gap as a function of kinetic energy in MeV. FIG. 7D shows proton time of flight difference per MeV of kinetic energy difference, as a function of proton kinetic energy in MeV.

Protons at proton therapy beam energies are non-relativistic, with their velocity a fraction of the speed of light as shown in FIG. 7A. They are also heavily ionizing in comparison with relativistic "minimum ionizing particles" or "mips" which deposit ~2 MeV/cm, as can been seen in FIG. 7B. Consequently, they may be efficiently detected and their time of flight precisely measured by detectors which are sensitive to charged particles and with have picosecond timing accuracy, such as Large Area Picosecond Photon Detectors ("LAPPDs") operating in ionization mode ("iLAPPDs"). These are described briefly below. Temporally and spatially coherent bunches of protons will coincide in each of these measures, with the time structure of their ionization measurements tracking the total ionization produced by the number of protons incident at their given energy, propagating across spatially separated detectors at their common velocity. Illustrative proton flight times for a detector spacing of 10 cm are illustrated in FIG. 7C, and the flight time sensitivity to variations in proton kinetic energy is shown in FIG. 7D for the same detector separation.

Spread or "dispersion" in this time structure is introduced when an ensemble of such protons, either collected into a set or associated within a spatially and temporally coherent proton "bunch", travel through material. The spread is caused by a combination of multiple Compton scattering causing different path lengths through the material (possibly with different stopping power along the different paths as well) resulting in different times-of-flight, as well as by "straggling" effects whereby different protons will stochastically experience different amounts of energy loss along a path because of differences in their multiple scattering interactions. One novel aspect of the presently disclosed technique is that it performs a residual energy measurement in proton radiography which is coherent across temporally and spatially localized photon bunches, yielding a measure both of the mean energy loss for the bunch and its variation.

An embodiment therefore makes use of Large Area Microchannel Plates (LAPPDs, which contain large area Micro Channel Plates or MCPs) operating in "ionization mode", i.e., with no photocathode. This maximizes device speed (provides narrowest pulses), minimizes device cost and maximizes radiation hardness (in each case by using no scintillator or photocathode). Protons at therapeutic proton beam energies are heavily ionizing, so that acceptable efficiency can be obtained. Segmentation of LAPPDs with delay-line strip readout very significantly reduces channel counts (and therefore costs and required readout time) while the very narrow (few nanosecond) pulses minimizes pile-up despite effectively "multiplexed" sub-millimeter two-dimensional imaging spatial resolution.

One example of a LAPPD is a LAPPD' Photosensor, which is manufactured by Incom, Inc. Readout is performed through dual-ended readout of thirty delay-line strips, using a custom application-specific integrated circuit and a custom data acquisition system based on programmable logic arrays. This device may be capable of single photoelectron time resolutions for a 20 cm×20 cm Micro Channel Plate (MCP) of better than 70 pSec FWHM, with spatial resolution of roughly 500 microns, and median gains higher than $10^7$. Multiple-photoelectron pulses show nanosecond pulse widths and timing resolution of <20 psec RMS, limited at present by detector analog bandwidth and sampling.

Similar results may be achievable with these devices operating in "ionization mode", i.e. through direct signal production by particles traversing an iMCP, which does not require a scintillator or photocathode. Particle detection by means of secondary emission of electrons at the MCP surface is employed. Given that treatment protons are considerably more heavily ionizing than are mips, it is believed that very accurate timing with high efficiency can be achieved for treatment protons measured by iMCPs in "iLAPPDs", particularly after energy loss in a patient as in a residual energy time-of-flight measurement.

The following references describe aspects of the above discussion in more detail:

[1] M. Minot et al., "Pilot Production & Commercialization of LAPPD", Nucl. Inst. Meth A787, July 2015, p. 78-84.
[2] E. Oberla et al., "A 15 GSa/s, 1.5 GHz Bandwidth Waveform Digitizing ASIC", Nucl. Inst. Meth. A735 (2014) 452-461.
[3] B. Adams et al., "Measurements of the Gain, Time Resolution, and Spatial Resolution of a 20×20 cm2 MCP-based Picosecond Photo-Detector", Nucl. Instr. Meth. A 732 (2013), 392-396.
[4] B. Adams et al., "A test facility for large-area microchannel plate assemblies using a pulsed sub-picosecond laser", Rev. Sci. Instrum. 84, 061301 (2013).
[5] L. Brianza et al., "Response of microchannel plates to single particles and to electromagnetic showers", Nucl. Instr. Meth. A797 (2015) 216-221.

Broadly, the disclosed technique makes use of time-of-flight measurements to characterize either initial or final proton energies either before or after passing through a patient (or other object) being imaged, either for single protons or in a common measurement for coherent (closely spaced in time) proton "bunches". It also makes use of proton time-of-flight transit times through a patient, which with knowledge of proton energies encode information bearing on the length of multiple-scattering-trajectories through the patient, again either for single protons or collectively for ensembles comprising proton beam pulse "bunches". Independently, it may make use of an imaging detector with submillimeter spatial resolution and efficient sensitivity to individual protons, and with either sub-nanosecond timing accuracy or with pulse widths of less than 5 nanoseconds.

The following are some advantages of the disclosed TOF-based approach:

Accuracy: Unlike calorimetry or range stack, time-of-flight determination of proton residual energy increases in absolute (not just relative) accuracy for protons of progressively lower energy.

Compactness: Imaging, tracking, and energy measurement functions can be combined, through the use of two spatially separated imaging time-of-flight detectors.

High Rate Capability: Time-of-flight detectors can use narrow pulses to minimize pile-up, and time-of-flight measurement electronics minimize dead time per channel. In particular, LAPPDs operating in ionization mode have extremely high rate capability.

Providing Additional Information: Time-of-flight measurement for individual protons or proton ensembles including timing measurements before and after traversing the patient provide additional information bearing on multiple-scattering path lengths and material traversed. This information may be incorporated into advanced reconstruction algorithms, thereby mitigating range mixing effects.

Cost-Effectiveness: Number of detectors and associated electronics readout channels are minimized by using time-of-flight measurement between a pair of detectors rather than instrumenting a stack of detectors or using an expensive calorimeter. The preferred embodiment incorporating LAPPDs operating in ionization mode provides cost-effective multiplexing through delay strip-line readout, obtaining submillimeter spatial resolution in two dimensions with drastically fewer electronics readout channels than a 2D sensor like a CMOS APS, and without requiring pairs of detectors like crossed scintillator strips.

Radiation Hardness: The preferred embodiment incorporating LAPPDs operating in ionization mode is significantly more radiation hard than prior art designs incorporating scintillators or semiconductor sensors.

Coherence for Bunches: Time-of-flight measurements for spatially localized ("pencil beam") temporally narrow (nanosecond scale width) proton bunches are performed in parallel by measuring the mean time delay for the pulses produced by the entire bunch. This is in contradistinction for calorimeters, which require single protons per bunch per RERD detector segment.

Alternatives

As described herein, one aspect of the disclosed approach is that of performing a time-of-flight measurement on significantly non-relativistic particles in the context of proton or light ion radiography (including proton or light ion computed tomography under the term "radiography"). Beyond the use of microchannel plates in ionization mode as described above, alternative embodiments may use other types of detectors, such as gas electron multipliers (GEMs, a technology distinct from MCPs) to accomplish fast timing with narrow pulses, with similarly or alternatively multiplexed readout to that we use with LAPPDs operating in ionization mode.

In addition, those skilled in the art will recognize alternative configurations incorporating time-of-flight measurement into proton radiography, including embodiments shown in FIGS. 8-10 and described below.

Figure 8:
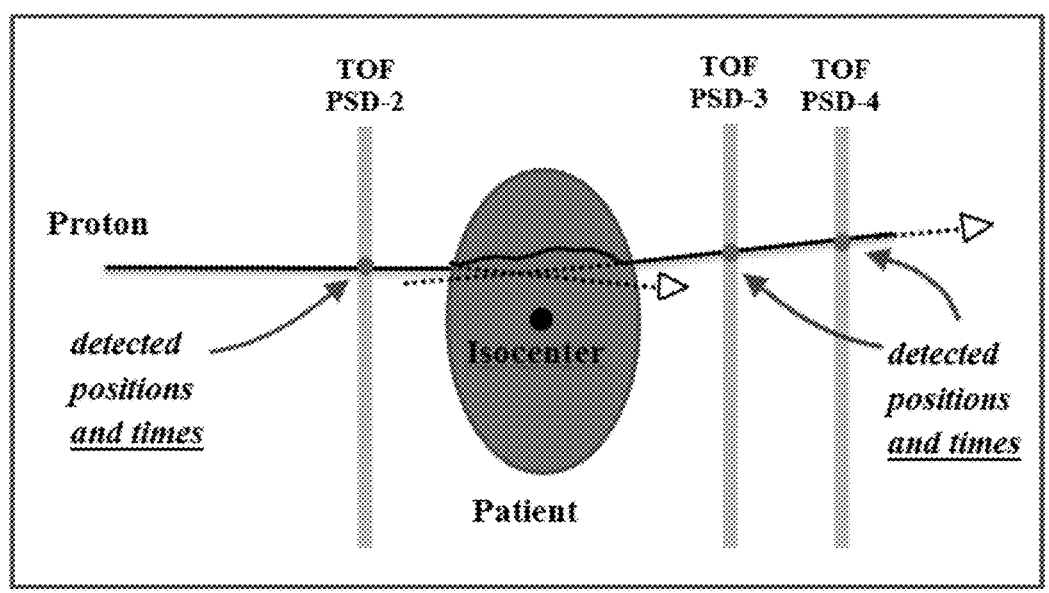
FIGS. 8-10 are schematic illustrations of proton radiography systems according to alternative embodiments.

FIG. 8 shows a time-of-flight proton radiography/proton CT system with one upstream time-of-flight imaging detector (TOF-PSD 2) and downstream combination imaging telescope and time-of-flight residual energy detector (TOF-PSD 3 and TOF-PSD 4). For a pencil beam active scanning proton delivery system, a single time of flight position sensitive detector may be used instead of the two-detector telescope configuration of FIG. 6, because the beam divergence is small.

The configuration of FIG. 8 may also be used either with single protons or with temporally and spatially coherently proton bunches. This can be used both for residual energy imaged measurement to complement spatial, temporal, and energetic beam modulation strategies, as well as to provide a measurement of ensemble average energy loss without requiring resolved individual protons as with a calorimeter. By using fast time-of-flight detectors with narrow pulse widths, the achievable readout rate (and hence reduction in time and dose associated with image acquisition) can far exceed what is possible with integrating approaches. Finally, by providing an additional dimension of finely-resolved spatial resolution in pulse shapes, one gains a means for preferentially weighting less-scattered proton paths without requiring explicit proton tracking.

Note that the same approach would also work using light ions, with still greater accuracy because of their lower velocities. Flight paths between upstream and downstream TOF-PSDs encode multiple path-integrated energy losses into time-of-flight delays which could be deconvolved from up/downstream timing distributions. It is understood by those skilled in the art that the TOF and PSD functions may be filled by two separate detectors operating in association with one another, and "TOF-PSD detector" will be taken as encompassing such arrangements.

Figure 9:
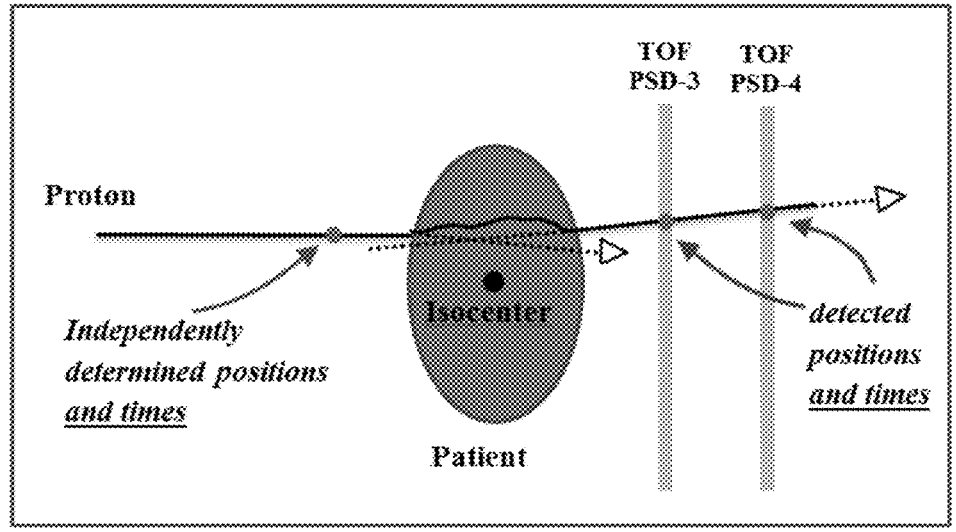

FIG. 9 shows another embodiment, one that eliminates both of the upstream TOF-PSD detectors. It is assumed that some other means is used of providing upstream timing and position information for the proton or protons. For a pencil beam active scanning proton delivery system, the beam time structure may be independently known or measured, as with the incident beam position. In this case, the upstream TOF-PSD detectors might be eliminated as shown.

The configuration of FIG. 9 may be used with either with single protons or with temporally and spatially coherently proton bunches. This can be used both for residual energy imaged measurement to complement spatial, temporal, and energetic beam modulation strategies, as well as to provide a measurement of ensemble average energy loss without requiring resolved individual protons as with a calorimeter. By using fast time-of-flight detectors with narrow pulse widths, the achievable readout rate (and hence reduction in time and dose associated with image acquisition) can far exceed what is possible with integrating approaches. Finally, by providing an additional dimension of finely-resolved spatial resolution in pulse shapes, one gains a means for preferentially weighting less-scattered proton paths without requiring explicit proton tracking.

Once again, an approach like that of FIG. 9 may also work using light ions, with still greater accuracy because of their lower velocities. Flight paths between upstream and downstream TOF-PSDs encode multiple path-integrated energy losses into time-of-flight delays which could be deconvolved from up/downstream timing distributions. It is understood by those skilled in the art that the TOF and PSD functions may be filled by two separate detectors operating in association with one another, and "TOF-PSD detector" will be taken as encompassing such arrangements.

Figure 10:
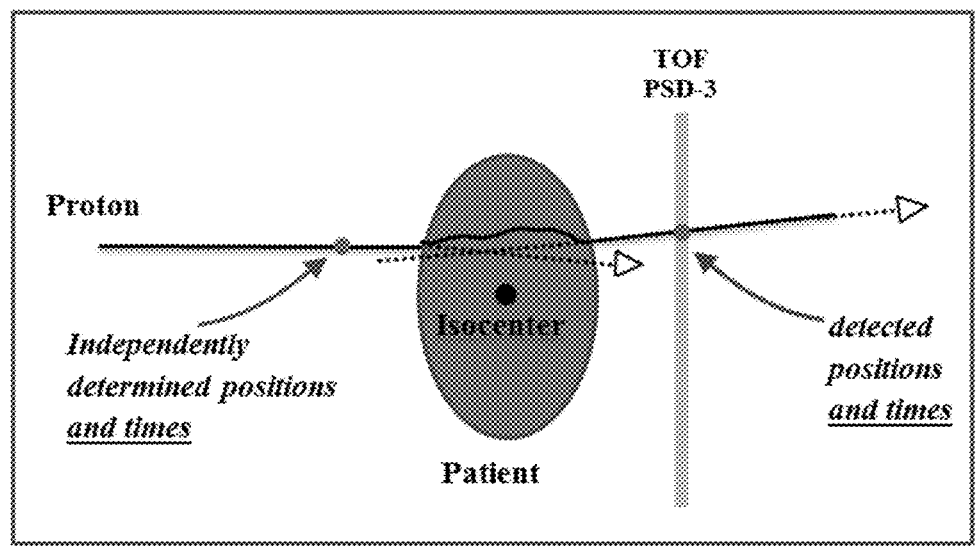

FIG. 10 shows another embodiment, one that eliminates both the upstream TOF-PSD detectors in favor of externally provided information, as well as eliminating one downstream TOF-PSD detector. For completeness, one could add additional configurations retaining downstream range stack or calorimeter detectors. For a pencil beam active scanning proton delivery system, the beam time structure may be independently known or measured, as with the incident beam position. In this case, the upstream TOF-PSD detectors might be eliminated as shown. As an alternative to measuring time-of-flight between paired detectors downstream of the patient, time-resolved ionization distributions can be measured by a single downstream time-of-flight position sensitive detector PSD-3.

Once again, the above configuration may be used with either with single protons or with temporally and spatially coherently proton bunches. This can be used both for residual energy imaged measurement to complement spatial, temporal, and energetic beam modulation strategies, as well as to provide a measurement of ensemble average energy loss without requiring resolved individual protons as with a calorimeter or range stack. By using fast time-of-flight detectors with narrow pulse widths, the achievable readout rate (and hence reduction in time and dose associated with image acquisition) can far exceed what is possible with integrating approaches. Finally, by providing an additional dimension of finely-resolved spatial resolution in pulse shapes, one gains a means for preferentially weighting less-scattered proton paths without requiring explicit proton tracking.

The disclosed technique is not limited to use with MCP-based detectors like LAPPDs. GEMS and other similar technology are also finely segmented spatially, and like LAPPDs have a finer mesh than the breadth of the incident proton beam (especially after beam broadening due to passage through material). Also, the protons are not necessarily incident along a path parallel to the pores (for efficiency reasons). The present signal readout is not fine-grained at the level of the pore granularity. LAPPDs have the benefit that the pulses they generate are much narrower than are generally provided by other detector types, including GEMs.

Other Applications

While this description focuses on application of proton radiography in support of proton radiation therapy (and the corresponding case for light ion therapy), other applications include non-destructive test and/or security applications (scanning objects of unknown internal structure/content).

Generalization

A system for non-relativistic ($b=v/c<0.8$) charged particle radiography that measures the energy loss of charged particles passing through an object while performing at least one time-of-flight measurement. The obtained energy loss information provides additional detail on target densities and stopping power when used with traditional radiographic techniques like photon or x-ray radiography. A probe beam consisting of nonrelativistic (<700 MeV/c, for protons) charged particles is passed through an object to be imaged, and in addition through one or more time-of-flight measurement detectors. The charged particles traverse physically separated detectors resulting in signals whose time separations are proportional to their path lengths and are inversely proportional to their velocities. From these velocities, given known charged particle types (and therefore masses), particle energies may be inferred. By rotating the object or rotating the source and detector about the object being imaged, tomographic radiography may be performed. By applying pulses of beam, discrete time-step movies of dynamic objects may be made.

While various embodiments have been particularly shown and described, it will be understood by those skilled in the art that various changes in form and details may be made therein without departing from the scope of the invention.

What is claimed is:

1. A proton radiography system, comprising:
    a source of a beam of protons at nonrelativistic energies, the beam to be directed on a beam path to an object to be imaged;
    one or more time-of-flight detectors arranged on the beam path, the time-of-flight detectors operative to detect incidence of protons of the beam and to generate respective output signals indicative thereof with a time resolution substantially less than a time of flight of the protons along the beam path; and
    a data acquisition and analysis subsystem coupled to the time-of-flight detectors to receive the respective output signals and (1) calculate one or more time-of-flight values for respective bunches of one or more protons, (2) convert the time-of-flight values to proton velocity values and corresponding proton energy values, and (3) use the proton energy values to calculate a corresponding value for a physical property of the object along the beam path, and incorporate the value of the physical property into a elements of a radiographic image of the object stored or displayed in the proton computed radiography system.

2. The proton radiography system of claim 1, wherein the detectors include an upstream pair of detectors between the source and the object, and a downstream pair of detectors downstream from the object, the upstream pair of detectors forming a first imaging telescope whose output signals indicate both location and timing of protons before encountering the object, the downstream pair of detectors forming a combination second imaging telescope and residual energy detector whose output signals indicate both location and timing of protons after encountering the object.

3. The proton radiography system of claim 2, wherein the first pair of detectors are first time-of-flight position-sensitive detectors, and the second pair of detectors are second time-of-flight position-sensitive detectors.

4. The proton radiography system of claim 3, wherein the first time-of-flight position-sensitive detectors and the second time-of-flight position-sensitive detectors are Large Area Picosecond Photon Detectors.

5. The proton radiography system of claim 4, wherein the Large Area Picosecond Photon Detectors include respective microchannel plates each having a large array of openings for passage of protons.

6. The proton radiography system of claim 5, wherein the microchannel plates are configured for operation in an ionization mode in which protons are detected by detecting secondary emission of electrons at respective surfaces of the microchannel plates.

7. The proton radiography system of claim 1, wherein the detectors include an upstream detector between the source and the object, and a downstream pair of detectors downstream from the object, the downstream pair of detectors forming a combination imaging telescope and time-of-flight residual energy detector whose output signals indicate both location and timing of protons after encountering the object.

8. The proton radiography system of claim 1, wherein the detectors include a downstream pair of detectors downstream from the object, the downstream pair of detectors forming a combination imaging telescope and time-of-flight residual energy detector whose output signals indicate both location and timing of protons after encountering the object.

9. The proton radiography system of claim 8, upstream timing and position information for the protons is provided without use of an upstream detector between the source and the object.

10. The proton radiography system of claim 1, wherein the detectors include a downstream detector downstream from the object, the downstream detector measuring time-resolved ionization distributions to generate output signals indicating both location and timing of protons after encountering the object.

11. A system for non-relativistic charged particle radiography that measures the energy loss of charged particles passing through an object while performing at least one time-of-flight measurement, comprising:
    a source of a probe beam of nonrelativistic charged particles directed along a beam path toward an object to be imaged;
    physically separated time-of-flight detectors generating respective output signals having time separations proportional to path lengths of the charged particles and inversely proportional to velocities if the charged particles; and
    a data acquisition and analysis subsystem configured and operative in response to the output signals of the time-of-flight detectors to calculate the velocities and respective particle energies.

12. A proton computed radiography detector system, comprising:
    means for determining energy and arrival time of a bunch of one or more of nonrelativistic charged particles on one side of an object to be imaged;
    one or more detectors with sub-nanosecond timing resolution on an opposite side of the object to be imaged; and
    a data acquisition and analysis subsystem configured and operative in response to output signals from the detectors to measure a parameter of the charged particles traversing the object being imaged.

13. A proton computed radiography detector system, comprising:
    means for determining energy of a bunch of one or more nonrelativistic charged particles on one side of an object to be imaged;
    one or more physically separated time-of-flight detectors with sub-nanosecond timing resolution on an opposite side of the object to be imaged; and
    a data acquisition and analysis subsystem configured and operative in response to output signals from the detectors to measure a parameter of the charged particles traversing the object being imaged.

14. A method, comprising:
    directing a beam of protons of nonrelativistic energies on a beam path to an object to be imaged;
    detecting incidence of protons of the beam at one or more detectors arranged on the beam path, and generating respective output signals indicative of the proton incidence with a time resolution substantially less than a time of flight of the protons along the beam path; and
    in response to respective output signals of the detectors, (1) calculating one or more time-of-flight values for respective bunches of one or more protons, (2) converting the time-of-flight values to proton velocity values and corresponding proton energy values, and (3)

using the proton energy values to calculate a corresponding value for a physical property of the object along the beam path, and incorporating the value of the physical property into a elements of a radiographic image of the object stored or displayed in a proton computed radiography system.

\* \* \* \* \*